(12) United States Patent
Saitoh et al.

(10) Patent No.: US 6,589,774 B2
(45) Date of Patent: Jul. 8, 2003

(54) PROCESS FOR PRODUCING A BRAN PICKLESS FLAVORING SOLUTION

(76) Inventors: Chiaki Saitoh, Ami-machi (JP); Atsushi Yashiro, Ami-machi (JP); Chikara Tokunaga, Ami-machi (JP); Kyoko Ozawa, Miho-mura (JP); Atsuko Yokoi, Tsukuba (JP); Nobuo Ogata, Tsuchiura (JP); Hiroshi Katahira, Akeno-machi (JP); Keiko Ochiai, Ebina (JP); Katsuhiko Ando, Machida (JP)

( * ) Notice: Subject to any disclaimer, the term of this patent is extended or adjusted under 35 U.S.C. 154(b) by 0 days.

(21) Appl. No.: 10/062,777

(22) Filed: Feb. 5, 2002

(65) Prior Publication Data

US 2002/0119514 A1 Aug. 29, 2002

Related U.S. Application Data

(62) Division of application No. 09/463,618, filed as application No. PCT/JP99/02854 on May 28, 1999, now Pat. No. 6,368,835.

(30) Foreign Application Priority Data

May 29, 1998 (JP) ............................................. 10-166226

(51) Int. Cl.$^7$ ................................................. C12N 1/20
(52) U.S. Cl. .................. 435/252.32; 435/843; 424/93.4
(58) Field of Search ........................... 435/252.32, 843; 424/93.4

(56) References Cited

U.S. PATENT DOCUMENTS

| 4,028,186 | A | * | 6/1977 | Sakai |
| 4,461,835 | A | * | 7/1984 | Sih |
| 4,476,139 | A | * | 10/1984 | Kempf et al. |
| 4,479,935 | A | * | 10/1984 | Metianu et al. |

FOREIGN PATENT DOCUMENTS

| JP | 59-39242 A | 3/1984 |
| JP | 59-39267 A | 3/1984 |
| JP | 8-242758 A | 9/1996 |

OTHER PUBLICATIONS

Derwent WPI, Publication No. 83050697, Publication Date: Nov. 11, 1983.
Derwent WPI, Publication No. 59039242, Publication Date: Mar. 3, 1984.
Derwent WPI, Publication No. 59039267, Publication Date: Mar. 3, 1984.
Derwent WPI, Publication No. 8242758, Publication Date: Sep. 24, 1996.
Paul J. Thomas, "Identification of Some Enteric Bacteria Which Convert Oleic Acid to Hydroxystearic Acid in Vitro", in *Gastroenterology*, vol. 62, No. 3 (1972), pp. 430–435.
Wallen, et al., "The Microbiological Production of 10–Hydroxystearic Acid from Oleic Acid", in *Archives of Biochemistry and Biophysics*, vol. 99, (1962), pp. 249–253.
Seo, et al., "Hydration of Squalene and Oleic Acid by Corynebacterium sp. S–401", *Agric. Biol. Chem.*, vol. 45, 9 (1981), pp. 2025–2030.
Derwent WPI, Publication No. 60066991, Publication Date: Apr. 17, 1985.
Derwent WPI, Publication No. 60100508, Publication Date: Jun. 1, 1985.
Derwent WPI, Publication No. 82056852, Publication Date: Dec. 1, 1982.

* cited by examiner

*Primary Examiner*—Michael V. Meller

(57) ABSTRACT

The present invention relates to a novel flavoring solution for making pickles having a flavor of foods pickled in rice bran paste (hereinafter referred to as a bran pickles flavoring solution), a clear bran pickles flavoring solution, processes for producing said solutions, a novel microorganism belonging to the genus Corynebacterium used for the production of said flavoring solutions, and a process for producing a solution containing a lactone wherein the lactone is selectively extracted from a culture of a lactone-producing microorganism. The present invention also relates to a novel bacterium of the genus Corynebacterium which has the ability to produce γ-dodecalactone and/or γ-dodecelactone and is useful for the production of said bran pickles flavoring solutions.

1 Claim, 1 Drawing Sheet

SEQUENCE LISTING

<160> NUMBER OF SEQ ID NOS: 1

<210> SEQ ID NO 1
<211> LENGTH: 1460
<212> TYPE: DNA
<213> ORGANISM: Corynebacterium sp.NK-1
<220> FEATURE:
<221> NAME/KEY: unsure
<222> LOCATION: (166)
<223> OTHER INFORMATION: n is "a" or "g" or "c" or "t".

<400> SEQUENCE: 1

| | | | | | | |
|---|---|---|---|---|---|---|
| ggttcaggac | ggaacgctgg | cggcgtgctt | aacacatgca | agtcgaacgg | aaaggccggg | 60 |
| tgcttgcacc | cggtactcga | gtggcgaacg | ggtgagtaac | acgtgggtga | tctgccctgc | 120 |
| acttcgggat | aagcctggga | aactgggtct | aataccggat | aggacnaccg | gttggtactg | 180 |
| gtggtggaaa | gttttcggt | gcaggatgag | ctcgcggcct | atcagcttgt | tggtgggta | 240 |
| atggcctacc | aaggcggcga | cgggtagccg | gcctgagagg | gtggacggcc | acattgggac | 300 |
| tgagacacgg | cccagactcc | tacgggaggc | agcagtgggg | aatattgcac | aatgggcgca | 360 |
| agcctgatgc | agcgacgccg | cgtggggat | gacggccttc | gggttgtaaa | ctcctttcaa | 420 |
| ccatgacgaa | gcttttgtga | cggtagtggt | agaagaagca | ccggctaact | acgtgccagc | 480 |
| agccgcggta | atacgtaggg | tgcgagcgtt | gtccggaatt | actgggcgta | aagagctcgt | 540 |
| aggtggtttg | tcgcgtcgtc | tgtgaaattc | cggggctcaa | ctccgggcgt | gcaggcgata | 600 |
| cgggcataac | ttgagtgctg | taggggagac | tggaattcct | ggtgtagcgg | tgaaatgcgc | 660 |
| agatatcagg | aggaacaccg | atggcgaagg | caggtctctg | ggcagtaact | gacgctgagg | 720 |
| agcgaaagca | tgggtagcga | acaggattag | ataccctggt | agtccatgcc | gtaaacggtg | 780 |
| ggcgctaggt | gtgggggtct | tccacgactt | ctgtgccgta | gctaacgcat | taagcgcccc | 840 |
| gcctggggag | tacggccgca | aggctaaaac | tcaaaggaat | tgacggggc | ccgcacaagc | 900 |
| cgcggagcat | gtggattaat | tcgatgcaac | gcgaagaacc | ttacctgggc | ttgacatgta | 960 |
| ccggatcggc | gcagagatgt | gtcttccctt | gtggtcggta | tacaggtggt | gcatggttgt | 1020 |
| cgtcagctcg | tgtcgtgaga | tgttgggtta | agtcccgcaa | cgagcgcaac | ccttgtcctg | 1080 |
| tgttgccagc | acgttgtggt | ggggactcac | gggagactgc | cggggttaac | tcggaggaag | 1140 |
| gtggggatga | cgtcaaatca | tcatgcccct | tatgtccagg | gcttcacaca | tgctacaatg | 1200 |
| gtcggtacag | tgggttgcta | caccgtgagg | tggtgctaat | ctcttaaagc | cggtctcagt | 1260 |
| tcggattgga | gtctgcaact | cgactccatg | aagtcggagt | cgctagtaat | cgcagatcag | 1320 |
| caatgctgcg | gtgaatacgt | tcccgggcct | tgtacacacc | gcccgtcacg | tcatgaaagt | 1380 |
| tggtaacacc | cgaagccggt | ggcccaaact | cgttagggag | ccgtcgaagg | tgggatcggc | 1440 |
| gattggacga | aatcctacaa | | | | | 1460 |

US 6,589,774 B2

PROCESS FOR PRODUCING A BRAN PICKLESS FLAVORING SOLUTION

CROSS REFERENCE TO RELATED APPLICATIONS

This application is a Divisional Application of application Ser. No 09/463,618, filed Jan. 28, 2000 now U.S. Pat. No. 6,368,835, which is a 371 of PCT/JP99/02854 filed May 28, 1999.

TECHNICAL FIELD

The present invention relates to a flavoring solution for making pickles having a flavor of foods pickled in rice bran paste (hereinafter referred to as a bran pickles flavoring solution), a clear bran pickles flavoring solution, processes for producing said flavoring solutions, a process for producing lactones which are essential components of said flavoring solutions, and a novel bacterium belonging to the genus Corynebacterium which is useful for producing a lactone.

BACKGROUND ART

It is common to make foods pickled in rice bran paste (hereinafter referred to as bran pickles) at home. However, in order to make bran pickles having a good flavor, a mature rice bran paste must be prepared by carrying out pickling of foods such as vegetables and stirring of the bran paste every day for more than several months. Thus, it takes a lot of efforts to take care of rice bran paste.

In order to obtain foods having a flavor of bran pickles without using bran paste, a method has been proposed which comprises pickling foods such as vegetables in a pickling solution having a flavor of bran pickles, and a study has been made on the aromatic components and seasoning components of a mature rice bran paste [Nippon Nogeikagaku Kaishi, 57, 1113 (1983)]. However, a flavoring substance essential to a desirable bran pickles flavoring solution has not been specified yet, and thus there has not been established an industrial process for producing a bran pickles flavoring solution containing such a compound at a high concentration.

As aromatic components of bran paste, γ-lactones such as γ-dodecalactone, γ-dodecelactone and γ-decalactone are considered to be important. As for the production of precursors of γ-lactones, it is known that a lactic acid bacterium [Gastroenterology, 62, 430 (1972)], a bacterium belonging to the genus Corynebacterium [Agricultural and Biological Chemistry, 45, 2025 (1981)], a bacterium belonging to the genus Pseudomonas [Archives of Biochemistry and Biophysics, 99, 249 (1962)], etc. are capable of producing γ-dodecalactone precursor (10-hydroxyoctadecanoic acid).

Also known is a method for converting ricinoleic acid into γ-decalactone using yeast belonging to the genus Saccharomyces, etc. to improve the quality of castor oil containing ricinoleic acid (Japanese Published Unexamined Patent Application No. 66991/85, Japanese Published Unexamined Patent Application No. 100508/85). Further, it is known that γ-lactones can be produced by fermentation using *Sporobolomyces oderus, Fusarium poae*, etc. separately.

A clear bran pickles flavoring solution is preferred from the standpoint of commercial value, because the image of a flavoring solution as a commercial product is improved and there is no need for removing suspended matters such as rice bran from the obtained pickles.

Previous methods for producing a clear bran pickles flavoring solution include a method which comprises fermenting a dispersed solution of rice bran (hereinafter referred to as a bran suspension) and subjecting the fermented bran suspension to solid-liquid separation by a filter press, a rotary filter or a centrifuge to obtain a separated solution as a bran pickles flavoring solution. According to such methods, a clear bran pickles flavoring solution can be obtained. However, fat-soluble aromatic components such as γ-lactones are removed together with the residue in these methods, and therefore, a desirable bran pickles flavoring solution can not be obtained.

Further, when a fermented bran suspension is extracted with an aqueous solution of ethanol and the obtained extract is mixed with the above separated solution to obtain a bran pickles flavoring solution, the fatty acids extracted with an aqueous solution of ethanol are precipitated and suspended in the mixture, making the resulting flavoring solution turbid. Thus, a clear bran pickles flavoring solution can not be obtained.

There have been reported a process for producing a bran pickling composition by fermentation using a lactic acid bacterium, yeast and a Gram-negative bacterium such as a bacterium belonging to the genus Pseudomonas (Japanese Published Examined Patent Application No. 56852/82) and a process for producing a bran pickling composition by collecting aromatic components of bran pickles by steam distillation and then adding the collected components to the flavoring material (Japanese Published Examined Patent Application No. 50697/83), but neither of them is effective for producing a clear bran pickles flavoring solution.

DISCLOSURE OF THE INVENTION

A need exists for a bran pickles flavoring solution useful for making good bran pickles, a clear bran pickles flavoring solution and establishment of processes for producing said flavoring solutions.

The present inventors have studied an industrial process for producing a bran pickles flavoring solution which can easily impart to pickles a mature flavor peculiar to bran pickles, specifically, a flavoring substance necessary for a bran pickles flavoring solution. As a result, the present inventors have found that propionic acid and γ-dodecalactone and/or γ-dodecelactone play an important role as bran pickles flavoring components, and after further studies, they have completed the present invention.

The present invention relates to the following (1)–(30). Hereinafter the following microorganisms are abbreviated as follows:

A microorganism having the ability to produce lactic acid; a lactic acid-producing bacterium.

A microorganism having the ability to produce propionic acid; a propionic acid-producing bacterium.

A microorganism having the ability to produce γ-dodecalactone and/or γ-dodecelactone; a γ-DD lactone-producing microorganism.

(1) A process for producing a bran pickles flavoring solution, which comprises culturing a lactic acid-producing bacterium, a propionic acid-producing bacterium and a γ-DD lactone-producing microorganism in a bran suspension or a dispersed solution of treated rice bran (hereinafter referred to as a treated bran suspension) to form propionic acid and γ-dodecalactone and/or γ-dodecelactone in the culture, said bran pickles flavoring solution comprising said culture.

(2) The process according to (1), wherein the culturing of the microorganisms is carried out by culturing two microorganisms respectively belonging to two groups arbitrarily selected from the three groups of lactic acid-producing bacteria, propionic acid-producing bacteria and γ-DD lactone-producing microorganisms in one bran suspension or treated bran suspension and separately culturing a microorganism belonging to the remaining group in another bran suspension or treated bran suspension, or by culturing separately three microorganisms respectively belonging to said three groups in a bran suspension or a treated bran suspension, and then the obtained cultures are mixed.

(3) The process according to (1), wherein the lactic acid-producing bacterium and the propionic acid-producing bacterium are cultured under anaerobic conditions and the γ-DD lactone-producing microorganism is cultured under aerobic conditions.

(4) The process according to (1), wherein the culturing of the microorganisms is carried out by culturing the γ-DD lactone-producing microorganism in the culture of the lactic acid-producing bacterium, and then culturing the propionic acid-producing bacterium in the obtained culture.

(5) The process according to (1), wherein the culturing of the microorganisms is carried out by culturing the propionic acid-producing bacterium in the culture of the lactic acid-producing bacterium, and separately culturing the γ-DD lactone-producing microorganism in the culture of the lactic acid-producing bacterium, and then the obtained cultures are mixed.

(6) The process according to (1), wherein the culturing of the γ-DD lactone-producing microorganism is carried out by culturing one kind of γ-DD lactone-producing microorganism under aerobic conditions and under anaerobic conditions separately, or by culturing one kind of γ-DD lactone-producing microorganism under aerobic conditions and culturing another kind of γ-DD lactone-producing microorganism under anaerobic conditions.

(7) The process according to any of (1)-(6), wherein the γ-DD lactone-producing microorganism is yeast.

(8) The process according to (7), wherein the yeast belongs to the genus Saccharomyces, Kluyveromyces or Zygosaccharomyces.

(9) The process according to any of (1)–(6), wherein the γ-DD lactone-producing microorganism is a bacterium belonging to the genus Corynebacterium.

(10) The process according to (9), wherein the bacterium belonging to the genus Corynebacterium is Corynebacterium sp. NK-1 (FERM BP-6329).

(11) The process according to any of (1)-(5), wherein the lactic acid-producing bacterium belongs to the genus Lactobacillus, Pediococcus, Leuconostoc, Streptococcus, Enterococcus or Bifidobacterium.

(12) The process according to any of (1)–(5), wherein the propionic acid-producing bacterium belongs to the genus Propionibacterium.

(13) The process according to (1), wherein the treated rice bran is prepared by treating rice bran with hydrolase.

(14) A bran pickles flavoring solution which is obtained by the process of any of (1)–(13).

(15) The bran pickles flavoring solution according to (14), which contains propionic acid in an amount of 500 ppm or more and γ-dodecalactone and/or γ-dodecelactone in an amount of 100 ppm or more as bran pickles flavoring components.

(16) A bran pickles flavoring solution which contains propionic acid in an amount of 500 ppm or more and γ-dodecalactone and/or γ-dodecelactone in an amount of 100 ppm or more as bran pickles flavoring components.

(17) A pickling solution for making pickles having a flavor of foods pickled in rice bran paste (hereinafter referred to as a bran pickling solution) which contains 50–3000 ppm propionic acid and 10–300 ppm γ-dodecalactone and/or γ-dodecelactone as bran pickles flavoring components.

(18) A process for producing a lactone, which comprises culturing a microorganism belonging to the genus Corynebacterium and having the ability to produce at least one γ-lactone selected from the group consisting of γ-dodecalactone, γ-dodecelactone and γ-decalactone in a medium containing at least one fatty acid selected from the group consisting of oleic acid, linoleic acid and ricinoleic acid to form at least one lactone selected from the group consisting of γ-dodecalactone, γ-dodecelactone and γ-decalactone in the culture, and then recovering the formed lactone from the culture.

(19) The process according to (18), wherein the microorganism is Corynebacterium sp. NK-1 (FERM BP-6329).

(20) Corynebacterium sp. NK-1 (FERM BP-6329).

(21) A clear bran pickles flavoring solution obtained by mixing:
  a) a separated solution obtained by subjecting the bran pickles flavoring solution of any of (14)–(16) to solid-liquid separation, or
  b) a separated solution obtained by culturing a lactic acid-producing bacterium and a propionic acid-producing bacterium in a bran suspension or a treated bran suspension, and then subjecting the obtained culture to solid-liquid separation; with
  c) an extract obtained by culturing a lactic acid-producing bacterium and a propionic acid-producing bacterium in a bran suspension or a treated bran suspension, subjecting the obtained culture to solid-liquid separation, and then extracting the obtained residue with an acidic aqueous solution of ethanol, or
  d) an extract obtained by culturing a γ-DD lactone-producing microorganism, subjecting the obtained culture to solid-liquid separation, and then extracting the obtained residue with an acidic aqueous solution of ethanol.

(22) A clear bran pickles flavoring solution which contains propionic acid in an amount of 500 ppm or more and γ-dodecalactone and/or γ-dodecelactone in an amount of 20 ppm or more as bran pickles flavoring components, and which has the turbidity of 0.4 or less at 660 nm when diluted 10 times with water.

(23) A clear bran pickling solution which contains 50–2000 ppm propionic acid and 1–150 ppm γ-dodecalactone and/or γ-dodecelactone as bran pickles flavoring components, and which has the turbidity of 0.4 or less at 660 nm.

(24) A process for producing a lactone-containing solution, which comprises subjecting a culture of a microorganism having the ability to produce a lactone to solid-liquid separation, recovering the residue, and then extracting the lactone from said residue with an acidic aqueous solution of ethanol. Herein the term lactone means all lactones such as γ-lactone and δ-lactone.

(25) The process according to (21) or (24), wherein the acidic aqueous solution of ethanol is in the pH range of 1.0–6.5.

(26) The process according to (21), (24) or (25), wherein the acidic aqueous solution of ethanol contains ethanol in an amount of 10 vol % or more.

(27) A process for producing pickles, which comprises pickling foods in the bran pickles flavoring solution or the bran pickling solution of any of (14)–(17) and (21)–(23).

(28) Pickles obtained by the process of (27).

(29) A seed strain for rice bran paste comprising a bacterium belonging to the genus Corynebacterium.

(30) A process for producing rice bran paste containing γ-dodecalactone and/or γ-dodecelactone, which comprises adding the seed strain for rice bran paste of (29) to rice bran paste.

The present invention is described below in detail.

Described first are a process for producing a novel bran pickles flavoring solution containing propionic acid and γ-dodecalactone and/or γ-dodecelactone, which comprises culturing a lactic acid-producing bacterium, a propionic acid-producing bacterium and a γ-DD lactone-producing microorganism in a bran suspension or a treated bran suspension; a novel bran pickles flavoring solution comprising the obtained culture; and a novel γ-DD lactone-producing microorganism, Corynebacterium sp. NK-1.

As the lactic acid-producing bacterium, any microorganism which has the ability to produce lactic acid and is applicable to foods can be used. For example, bacteria belonging to the genus Lactobacillus, Pediococcus, Leuconostoc, Streptococcus, Enterococcus or Bifidobacterium can be used. The preferred bacteria are those belonging to the species *Lactobacillus plantarum, Pediococcus pentosaceus, Leuconostoc mesenteroides, Streptococcus lactis, Streptococcus thermophilus, Streptococcus cremoris, Enterococcus faecalis* and *Bifidobacterium bifidum*. Particularly preferred are those of the species *Lactobacillus plantarum* and *Enterococcus faecalis*.

As the propionic acid-producing bacterium, any microorganism which has the ability to produce propionic acid and is applicable to foods can be used. Preferred are bacteria belonging to the genus Propionibacterium used for producing cheese, etc., for example, bacteria belonging to the species *Propionibacterium freudenreichii* and *Propionibacterium thoenii*.

As the γ-DD lactone-producing microorganism, any microorganism which has the ability to produce γ-dodecalactone and/or γ-dodecelactone and is applicable to foods can be used. Preferred are yeast and bacteria belonging to the genus Corynebacterium.

Examples of the γ-DD lactone-producing yeast are those belonging to the genus Saccharomyces, Kluyveromyces or Zygosaccharomyces. Preferred are yeasts belonging to the species *Saccharomyces cerevisiae, Saccharomyces uvarum, Saccharomyces exigus, Kluyveromyces lactis, Kluyveromyces marxianus, Kluyveromyces thermotolerans, Zygosaccharomyces bailii* and *Zygosaccharomyces florentinus*.

As the bacterium belonging to the genus Corynebacterium, Corynebacterium sp. NK-1 is preferably used.

Corynebacterium sp. NK-1 was isolated from bran paste. The microbiological properties of this strain and the basis for identification are described below.

(A) Morphological Characteristics
 1)
  Morphology of cells: Short rod
  Size: 1.0–1.2×0.8–1.0 μm
 2) Polymorphism of cells: Not observed
 3) Motility: Not observed
 4) Sporulation: Not observed (B) Cultural Characteristics
The cultural characteristics of the strain when cultured on a bouillon-agar plate medium and in a bouillon-liquid medium are shown below.
 1) Culturing on a bouillon-agar plate medium (1–2 days of culturing)
  a) Growth: Abundant
  b) Color: Cream
  c) Gloss: Observed
  d) Diffusible pigments: Negative
 2) Culturing in a bouillon-liquid medium (1–2 days of culturing)
  a) Growth on the surface: None
  b) Turbidity: Positive
 3) Stab culture in a bouillon-gelatin medium
  a) Growth: Abundant
  b) Liquefaction of gelatin: Positive
 4) Litmus-milk reaction
  a) Reaction: Alkali
  b) Coagulation: Negative
  c) Liquefaction: Negative (C) Physiological Properties
 1) Gram staining: Positive
 2) Nitrate reduction:
  Positive in a bouillon medium
  Negative in a succinic acid medium
 3) Denitrification reaction: Negative
 4) MR test: Negative
 5) VP test: Negative
 6) Indole production: Negative
 7) Hydrogen sulfide production: Positive
 8) Hydrolysis of starch: Negative
 9) Utilization of citric acid: Positive in Koser's medium
 10) Utilization of inorganic nitrogen sources
  a) Nitrates: Positive
  b) Ammonium salts: Positive
 11) Pigment production: None
 12) Urease: Positive
 13) Oxidase: Negative
 14) Catalase: Positive
 15) Growth range
  a) pH range for growth: pH 5–11 (optimum pH: around pH 6)
  b) Temperature range for growth: 11–45° C. (optimum temperature: around 29° C.)
 16) Attitude toward oxygen: Aerobic
 17) O-F test: Oxidative
 18) Acid production (aerobic conditions)
 Growth was not observed by stationary culture. The results obtained by shaking culture are shown below.
 +: Produced −: Not produced
  a) L-Arabinose: −
  b) D-Xylose: −
  c) D-Glucose: +
  d) D-Mannose: −
  e) D-Fructose: +
  f) D-Galactose: −
  g) Maltose: −
  h) Sucrose: −
  i) Lactose: −
  j) Trehalose: −
  k) D-Sorbitol: −
  l) D-Mannitol: −
  m) Inositol: −
  n) Glycerin: −
  o) Starch: −

(D) Chemotaxonomic Properties
  1) DNA base composition (G+C mol %): 69.3
  2) Cellular lipids
    Major quinone: MK-9 (H2)
    Major fatty acid: C16:0
    Mycolic acid: Coryneform
  3) Diamino acid composition of
    cell wall peptidoglycan: meso-A2pm
(E) Other Properties The base sequence of 16S ribosome RNA (16S rRNA) gene is shown by SEQ ID NO: 1 in the Sequence Listing.

Taxonomical studies were made on the strain based on the above microbiological properties referring to the descriptions in Bergey's Manual of Systematic Bacteriology, vol. 2 (1986), whereby the strain was presumed to be a bacterium related to the genus Corynebacterium. Further, the base sequence of 16S rRNA was determined and molecular genealogical analysis was carried out on the base sequence of 16S rRNA by the neighbor joining method using the base sequences of microorganisms of the genus Corynebacterium and its related genera as the reference sequences. As a result, the strain was classified in the genus Corynebacterium.

The strain was thus identified as a bacterium belonging to the genus Corynebacterium and was named Corynebacterium sp. NK-1.

This strain was deposited with the National Institute of Bioscience and Human-Technology, Agency of Industrial Science and Technology, Ministry of International Trade and Industry (1–3, Higashi 1-chome, Tsukuba-shi, Ibaraki-ken, Japan) on Apr. 23, 1998 with accession number FERM BP-6329.

The deposited strain has been accepted for deposit under the Budapest Treaty on the International Recognition of the Deposit of Microorganisms for the Purpose of Patent Procedure. All restrictions on the availability to the public of the deposited strain will be irrevocably removed upon the issuance of a patent.

In the process for producing a bran pickles flavoring solution according to the present invention, culturing of the lactic acid-producing bacterium, the propionic acid-producing bacterium and the γ-DD lactone-producing microorganism may be carried out by inoculating these microorganisms together in a bran suspension or a treated bran suspension as a medium, or by culturing first the lactic acid-producing bacterium and then the propionic acid-producing bacterium or the γ-DD lactone-producing microorganism, and subsequently culturing the remaining microorganism.

Alternatively, each of the above three microorganisms may be cultured individually, or any one of the above microorganisms and the other two microorganisms may be cultured separately in a bran suspension or a treated bran suspension, and after the culturing, the obtained cultures may be mixed.

Further, it is possible to employ two or more kinds of microorganisms which can produce the same substance. The order of culturing, the combination of microorganisms and the kind of culturing can be arbitrarily selected.

When the γ-DD lactone-producing microorganism is cultured under aerobic conditions, γ-dodecalactone and/or γ-dodecelactone is produced. On the other hand, when it is cultured under anaerobic conditions, production of γ-dodecalactone and/or γ-dodecelactone is suppressed, but the resulting culture has a good flavor. Thus, a culture having a preferable flavor can be obtained by culturing the γ-DD lactone-producing microorganism under aerobic conditions and anaerobic conditions, respectively, and then mixing the obtained cultures.

As the medium of the present invention, a suspension which is prepared by dispersing rice bran or treated rice bran in water at a concentration of 1–70 vol % may be employed.

As the rice bran, not only fresh rice bran, but also roasted rice bran and steamed rice bran can be used.

Examples of the treated rice bran include treated matters obtained by decomposing components of rice bran with various enzymes. Suitable enzymes include hydrolase enzymes such as a lipid-hydrolyzing enzyme (e.g. lipase), a protein-hydrolyzing enzyme (e.g. protease and peptidase) and a starch-hydrolyzing enzyme (e.g. amylase and glucoamylase).

The enzymatic treatment is carried out by adding an enzyme to a bran suspension and subjecting the mixture to reaction at 30–60° C. for 1–20 hours.

In the above culturing and enzymatic treatment of rice bran, vegetables or extracts thereof, marine products or extracts thereof, yeast extract, protein hydrolysate, starch hydrolysate, glucose, etc. may be added, if necessary.

Propionic acid-producing bacteria require lactic acid to produce propionic acid. Therefore, when the propionic acid-producing bacterium employed can not produce enough lactic acid, it is necessary that lactic acid be contained in the medium. In cases where the propionic acid-producing bacterium which does not produce enough lactic acid is cultured in a culture broth of the lactic acid-producing bacterium or is cultured together with the lactic acid-producing bacterium, there is no need to add lactic acid to the medium. However, in cases where lactic acid does not exist or is not produced in a medium, lactic acid must be added to the medium.

When the γ-DD lactone-producing microorganism is yeast, precursors of γ-dodecalactone and/or γ-dodecelactone are required. Thus, it is necessary to add precursors of γ-dodecalactone and/or γ-dodecelactone such as 10-hydroxyoctadecanoic acid and 10-hydroxyoctadecenoic acid to the medium. In cases where the γ-DD lactone-producing microorganism is cultured in a culture broth of the lactic acid-producing bacterium or is cultured together with the lactic acid-producing bacterium, precursors of γ-dodecalactone and/or γ-dodecelactone are formed from oleic acid and linoleic acid in the medium by the action of the lactic acid-producing bacterium, and so there is no need to add said precursors to the medium.

When the γ-DD lactone-producing microorganism is a bacterium belonging to the genus Corynebacterium, it is necessary that oleic acid and linoleic acid be contained in the medium. However, as rice bran contains these fatty acids, there is no need for addition thereof. By culturing said bacterium in a bran suspension or treated rice bran, γ-dodecalactone and/or γ-dodecelactone can be formed and accumulated in the culture.

Culturing of the three kinds of microorganisms is carried out usually at 10–37° C. and completed in 1–20 days, whereby propionic acid and γ-dodecalactone and/or γ-dodecelactone can be formed and accumulated in the culture.

Culturing of the lactic acid-producing bacterium and the propionic acid-producing bacterium is preferably carried out under anaerobic conditions, for example, by stationary culture. Culturing of the yeast and the bacterium belonging to the genus Corynebacterium is preferably carried out under aerobic conditions, for example, by shaking culture or submerged spinner culture under aeration.

The culture obtained by the culturing is used, as such, as a bran pickles flavoring solution. As the bran pickles flavoring solution, those which contain, as flavoring components, propionic acid in an amount of 500 ppm or more, preferably 1000 ppm or more, and γ-dodecalactone and/or γ-dodecelactone in an amount of 100 ppm or more, preferably 250 ppm or more are desirable in respect of bran pickles flavor. The bran pickles flavoring solutions which further contain 0.1–10.0 wt % lactic acid and 3.0–20.0 wt % sodium chloride are more desirable in respect of bran pickles flavor. It is preferred that sodium chloride is contained at the above concentration also from the standpoint of preservation.

The bran pickles flavoring solution, as such, can be used as a bran pickling solution, or may be diluted with water, etc. to prepare a bran pickling solution containing 50–3000 ppm propionic acid and 10–300 ppm γ-dodecalactone and/or γ-dodecelactone. The bran pickling solution may further contain additives such as lactic acid, sodium chloride and sodium glutamate.

The clear bran pickles flavoring solution of the present invention is described below.

The clear bran pickles flavoring solution of the present invention is obtained by mixing the following separated solution with the following extract.

Examples of the separated solution include a separated solution obtained by subjecting the above bran pickles flavoring solution to solid-liquid separation, and a separated solution obtained by culturing the lactic acid-producing bacterium and the propionic acid-producing bacterium in a bran suspension or a treated bran suspension and then subjecting the obtained culture to solid-liquid separation.

Examples of the extract include an extract obtained by subjecting the above bran pickles flavoring solution to solid-liquid separation and then extracting the obtained residue with an acidic aqueous solution of ethanol, and an extract obtained by culturing the γ-DD lactone-producing microorganism described below in a medium, subjecting the obtained culture to solid-liquid separation, and then extracting the obtained residue with an acidic aqueous solution of ethanol.

The separated solution and the residue can be obtained by subjecting the bran pickles flavoring solution or the culture to solid-liquid separation. The solid-liquid separation can be effected by any conventional method, for example, methods using a filter press, a rotary filter, a centrifuge, a dynamic filter, etc. Extraction of γ-dodecalactone and/or γ-dodecelactone from the residue is carried out repeatedly with an acidic aqueous solution of ethanol, and γ-dodecalactone and/or γ-dodecelactone can be selectively extracted from the residue.

The pH of the acidic aqueous solution of ethanol for use is 1.0–6.5, preferably 2.0–6.0 and the concentration of ethanol in the solution is 10 vol % or more, preferably 30 vol % or more. The pH adjustment is usually carried out by using lactic acid, hydrochloric acid or a culture of a lactic acid-producing bacterium. Extraction of lipids such as fatty acids in the culture can be suppressed by making the aqueous solution of ethanol acidic. By suppression of extraction of said lipids, the cause of turbidity at the time of preparing a bran pickles flavoring solution can be reduced remarkably, which enables the production of a good clear bran pickles flavoring solution.

Described below is a method of culturing a γ-DD lactone-producing microorganism in order to produce the clear bran pickles flavoring solution.

As the γ-DD lactone-producing microorganism, any microorganism which has the ability to produce γ-dodecalactone and/or γ-dodecelactone can be used. Any of the γ-DD lactone-producing microorganisms used for the production of the above bran pickles flavoring solution may be employed.

As the medium, any natural or synthetic medium which contains oleic acid and linoleic acid, and also carbon sources, nitrogen sources, inorganic salts, etc. capable of being assimilated by the lactone-producing microorganism can be used as well as a bran suspension and treated rice bran.

When the γ-DD lactone-producing microorganism is yeast, precursors of γ-dodecalactone and/or γ-dodecelactone are required. Thus, it is necessary to add said precursors, for example, 10-hydroxyoctadecanoic acid and 10-hydroxyoctadecenoic acid to the medium.

In cases where the γ-DD lactone-producing microorganism is cultured in a culture broth of the lactic acid-producing bacterium or is cultured together with the lactic acid-producing bacterium, precursors of γ-dodecalactone and/or γ-dodecelactone are formed from oleic acid and linoleic acid in the medium by the action of the lactic acid-producing bacterium, and so there is no need to add said precursors to the medium.

Examples of the carbon sources include carbohydrates such as glucose, fructose, sucrose, molasses, starch and starch hydrolysate, organic acids such as acetic acid and propionic acid, and alcohols such as ethanol and propanol.

Examples of the nitrogen sources include ammonia, ammonium salts of inorganic or organic acids such as ammonium chloride, ammonium sulfate, ammonium acetate and ammonium phosphate, and other compounds containing nitrogen, as well as peptone, meat extract, yeast extract, corn steep liquor, casein hydrolysate, soybean cake, soybean cake hydrolysate, and various fermented cells and digested matters thereof. Examples of the inorganic substances include potassium dihydrogenphosphate, dipotassium hydrogenphosphate, magnesium phosphate, magnesium sulfate, sodium chloride, ferrous sulfate, manganese sulfate, copper sulfate and calcium carbonate.

Preferred sources of fatty acids to be supplied to the medium include rice bran, hydrolase-treated rice bran, a product of hydrolysis of food fat containing linoleic acid and oleic acid such as animal fat, vegetable fat or milk fat, and a mixture obtained by adding to said hydrolysis product a food protein such as milk protein or vegetable protein at the rate of 0.1–1.0 by weight.

The culturing is usually carried out under aerobic conditions, for example, by shaking culture or submerged spinner culture under aeration, at pH 3–9 at 15–40° C. for 2–7 days.

The clear bran pickles flavoring solution obtained by the above process contains propionic acid in an amount of 500 ppm or more, preferably 1000 ppm or more, and γ-dodecalactone and/or γ-dodecelactone in an amount of 20 ppm or more, preferably 40 ppm or more, as flavoring components, and has the turbidity of 0.4 or less, preferably 0.2 or less at 660 nm when diluted 10 times with water.

The clear bran pickles flavoring solution, as such, can be used as a clear bran pickling solution, or if necessary, may be diluted with water, etc. to prepare a clear bran pickling solution containing 50–2000 ppm propionic acid and 1–150 ppm γ-dodecalactone and/or γ-dodecelactone. The clear bran pickling solution may further contain additives such as lactic acid, sodium chloride and sodium glutamate.

The bran pickles flavoring solution and the bran pickling solution, whether clear or not, may additionally comprise, as may be appropriate, additives such as a seasoning (e.g. sodium glutamate), starch hydrolysate, a sugar (e.g. glucose and sucrose), protein hydrolysate, yeast extract, vegetable extract, marine product extract, and an organic acid (e.g. lactic acid, acetic acid and succinic acid), as well as spice such as red pepper, Japanese pepper and citron.

Pickles having a flavor of good bran pickles can be obtained by pickling foods such as vegetables, seafoods and meat in the bran pickling solution, whether clear or not, or sprinkling the bran pickling solution over foods, etc.

Described below is a novel process for producing at least one γ-lactone selected from the group consisting of γ-dodecalactone, γ-dodecelactone and γ-decalactone (hereinafter collectively referred to as γ-lactones) by the use of a bacterium belonging to the genus Corynebacterium.

As the bacterium belonging to the genus Corynebacterium of the present invention, any bacterium which has the ability to form γ-dodecalactone from oleic acid, γ-dodecelactone from linoleic acid or γ-decalactone from ricinoleic acid can be used. An example of such a strain is Corynebacterium sp. NK-1 described above.

As for the medium and the method of culturing, those used for culturing the above γ-DD lactone-producing microorganism are applicable except that addition of ricinoleic acid to the medium is necessary.

Recovery of γ-lactones from the culture obtained by culturing is carried out, for example, by column chromatography.

Described below is a method of extracting a lactone from a fermentation broth obtained by culturing a lactone-producing microorganism.

As the lactone-producing microorganism, any microorganism having the ability to produce at least one of the γ-lactones and δ-lactones can be used. Useful microorganisms include the γ-DD lactone-producing microorganisms used for producing the above bran pickles flavoring solution. As the method of extracting a lactone from the culture, the same method as that used for producing the above clear bran pickles flavoring solution is applicable.

That is, the residue is obtained by subjecting the culture to solid-liquid separation. The solid-liquid separation can be effected by any of the above methods. A lactone can be selectively extracted from the residue by repeating extraction using an acidic aqueous solution of ethanol.

The pH of the acidic aqueous solution of ethanol for use is 1.0–6.5, preferably 2.0–6.0 and the concentration of ethanol in the solution is 10 vol % or more, preferably 30 vol % or more. The pH adjustment is usually carried out by using lactic acid or hydrochloric acid. Extraction of lipids such as fatty acids in the culture can be suppressed by making the aqueous solution of ethanol acidic.

The seed strain for rice bran paste of the present invention is described below.

The seed strain for rice bran paste is characterized in that it comprises a bacterium belonging to the genus Corynebacterium which has the ability to produce γ-dodecalactone and/or γ-dodecelactone.

Usually in rice bran paste exist lactic acid bacteria, and it is known that propionic acid is accumulated in rice bran paste even in the absence of a propionic acid bacterium. Therefore, the seed strain for rice bran paste of the present invention only needs to contain, as an essential component, a bacterium belonging to the genus Corynebacterium which is capable of producing γ-dodecalactone and/or γ-dodecelactone. If necessary, a lactic acid-producing bacterium or a propionic acid-producing bacterium may be added.

The bacterium belonging to the genus Corynebacterium, the lactic acid bacterium and the propionic acid bacterium useful for the seed strain are the same as those useful in the above process for producing the bran pickles flavoring solution of the present invention.

Examples of the rice bran paste to which the above seed strain is added include fresh rice bran and a mixture of fresh rice bran and roasted rice bran or steamed rice bran, which may comprise vegetables or extracts thereof, marine products or extracts thereof, yeast extract, protein hydrolysate, etc.

Addition of the above seed strain to such bran paste causes fermentation to form propionic acid and γ-dodecalactone and/or γ-dodecelactone in the bran paste, whereby bran paste which is useful for making pickles having an excellent flavor of bran pickles can be obtained.

BEST MODES FOR CARRYING OUT THE INVENTION

Figure 1:
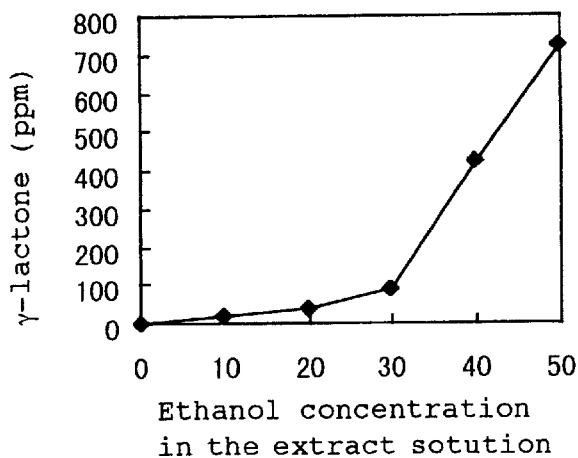
FIG. 1 is a graph showing the concentration of ethanol in the solution used for extraction and the concentration of extracted γ-lactone.

Certain specific embodiments of the present invention are illustrated in the following examples. In the examples, % means wt % unless otherwise specified.

EXAMPLE 1

A dispersed solution prepared by mixing rice bran (Tajimaya) with water at a concentration of 10% (referred to as a 10% bran suspension) was heated to 85° C. and then cooled to 50° C. To the bran suspension were added protease (Novo Nordisk A/S), peptidase (Novo Nordisk A/S), amylase (Nagase Seikagaku Co., Ltd.), glucoamylase (Nagase Seikagaku Co., Ltd.) and lipase (Amano Pharmaceutical Co., Ltd.) which are suitable for use in food processing in an amount of 0.1% based on the rice bran, followed by reaction at 50° C. for 3 hours. After the reaction was completed, the reaction mixture was sterilized by heating at 120° C. for 15 minutes. *Lactobacillus plantarum* was inoculated therein as a lactic acid bacterium, followed by stationary culture at 25° C. for 2 days. Then, *Saccharomyces cerevisiae* was inoculated therein as a γ-DD lactone-producing yeast, followed by spinner culture under aeration at 25° C. for 4 days. After the culturing was completed, fermented lactic acid (90% lactic acid, Musashino Shoji Co., Ltd.) was added to the obtained culture in an amount of 2% based on said culture, and *Propionibacterium freudenreichii* was inoculated therein as a propionic acid-producing bacterium, followed by stationary culture at 25° C. for 7 days.

After the culturing was completed, the obtained culture was sterilized by heating at 95° C. for 30 minutes. The amounts of propionic acid, γ-dodecalactone and γ-dodecelactone in said culture were determined. The amount of propionic acid was determined by capillary electrophoresis (HP 3D CE, Hewlett Packard). The amounts of γ-dodecalactone and γ-dodecelactone were determined by means of a mass spectrum detector (QP5000, Shimadzu Corporation) after extraction from said culture with a pentane/ether mixture (1:1) using cyclohexanol as an internal standard and separation by gas chromatography. As a result, it was found that said culture contained 1.1% propionic acid, 0.11% γ-dodecalactone and 0.07% γ-dodecelactone, and also had a flavor of mature bran pickles.

The obtained culture, which is a bran pickles flavoring solution, was diluted 10 times with water, and lactic acid, sodium chloride and sodium glutamate were added thereto to the concentrations of 0.5%, 2.5% and 0.62%, respectively, to prepare a pickling solution (solution of the present invention). In this pickling solution were pickled cucumbers which had been previously pickled in a 6% aqueous solution of sodium chloride at 5° C. for one day. Separately, a commercially available bran pickles flavoring solution (hereinafter referred to as commercial solution 1) was diluted according to the attached description, and cucumbers were pickled in the resulting pickling solution in the same manner as above. After pickling at 5° C. for 2 days, the pickling solution was removed and the pickled cucumbers were sliced. Evaluation of the sliced cucumbers was made in respect of mature flavor, bran pickles flavor and desirability as bran pickles by 12 panelists each having 7 points on each quality.

The results are shown in Table 1.

TABLE 1

|  | Mature flavor | Bran pickles flavor | Desirability as bran pickles |
|---|---|---|---|
| Solution of the present inv. | 5.11 ± 1.45 | 5.00 ± 1.01 | 4.97 ± 1.11 |
| Commercial solution 1 | 3.12 ± 1.16 | 2.89 ± 1.21 | 2.16 ± 1.46 |

As shown in Table 1, the solution of the present invention gave pickles superior to those obtained by using commercial solution 1 in all of the above qualities, i.e. mature flavor, bran pickles flavor and desirability as bran pickles.

EXAMPLE 2

After a 10% bran suspension was treated with enzymes and sterilized by heating in the same manner as in Example 1, *Enterococcus faecalis* was inoculated therein as a lactic acid bacterium, followed by stationary culture at 25° C. for 2 days. After the culturing was completed, the obtained culture was divided into two equal portions. Into one portion was inoculated *Zygosaccharomyces bailii* as a γ-DD lactone-producing yeast, followed by spinner culture under aeration for 5 days. Into the other portion was inoculated *Propionibacterium freudenreichii* as a propionic acid-producing bacterium, followed by stationary culture for 5 days. After the culturing was completed, both cultures were sterilized by heating at 95° C. for 30 minutes and sodium chloride was added thereto in an amount of 5%, followed by mixing of the cultures. The obtained mixture had a flavor of mature bran pickles and contained 1.2% propionic acid, 0.08% γ-dodecalactone and 0.09% γ-dodecelactone.

Cucumbers were pickled in an aqueous solution prepared by diluting said mixture 10 times (solution of the present invention) and in a commercially available bran pickles flavoring solution (commercial solution 1) according to the method described in Example 1, and evaluation of the pickled cucumbers was made in respect of the same qualities by 12 panelists each having 7 points on each quality.

The results are shown in Table 2.

TABLE 2

|  | Mature flavor | Bran pickles flavor | Desirability as bran pickles |
|---|---|---|---|
| Solution of the present inv. | 4.84 ± 1.36 | 4.79 ± 1.21 | 5.00 ± 1.15 |
| Commercial solution 1 | 2.67 ± 1.45 | 3.11 ± 1.33 | 2.22 ± 1.51 |

As shown in Table 2, the solution of the present invention gave pickles superior to those obtained by using commercial solution 1 in all of the evaluated qualities, i.e. mature flavor, bran pickles flavor and desirability as bran pickles.

EXAMPLE 3

After a 10% bran suspension was treated with enzymes and sterilized by heating in the same manner as in Example 1, *Lactobacillus plantarum* was inoculated therein as a lactic acid-producing bacterium, followed by stationary culture at 25° C. for 2 days. Further, *Propionibacterium freudenreichii* was inoculated therein as a propionic acid-producing bacterium, followed by stationary culture at 25° C. for 7 days. Separately, a 10% bran suspension was treated with enzymes and sterilized by heating in the same manner as in Example 1, and a γ-DD lactone-producing microorganism Corynebacterium sp. NK-1 was inoculated therein, followed by spinner culture under aeration for 5 days. After the culturing was completed, both cultures were mixed. The obtained mixture had a flavor of mature bran pickles and contained 0.7% propionic acid, 0.08% γ-dodecalactone and 0.06% γ-dodecelactone.

Cucumbers were pickled in an aqueous solution prepared by diluting said mixture 10 times (solution of the present invention) and in a commercially available bran pickles flavoring solution (commercial solution 1) according to the method described in Example 1, and evaluation of the pickled cucumbers was made in respect of the same qualities by 12 panelists each having 7 points on each quality.

The results are shown in Table 3.

TABLE 3

|  | Mature flavor | Bran pickles flavor | Desirability as bran pickles |
|---|---|---|---|
| Solution of the present inv. | 5.24 ± 1.19 | 5.31 ± 1.00 | 5.02 ± 0.92 |
| Commercial solution 1 | 2.97 ± 1.21 | 2.99 ± 1.13 | 2.32 ± 1.52 |

As shown in Table 3, the solution of the present invention gave pickles superior to those obtained by using commercial solution 1 in all of the evaluated qualities, i.e. mature flavor, bran pickles flavor and desirability as bran pickles.

EXAMPLE 4

After a 10% bran suspension was treated with enzymes and sterilized by heating in the same manner as in Example 1, *Lactobacillus plantarum* was inoculated therein as a lactic acid-producing bacterium, followed by stationary culture at 25° C. for 2 days.

Separately, a 10% bran suspension was treated with enzymes and sterilized by heating in the same manner as in Example 1, and *Lactobacillus plantarum* was inoculated therein as a lactic acid-producing bacterium, followed by stationary culture at 25° C. for 2 days. Further, *Propionibacterium freudenreichii* was inoculated therein as a propionic acid-producing bacterium, followed by stationary culture at 25° C. for 7 days.

Another 10% bran suspension was treated with enzymes and sterilized by heating in the same manner as in Example 1, and *Lactobacillus plantarum* was inoculated therein as a lactic acid-producing bacterium, followed by stationary culture at 25° C. for 2 days. Further, *Saccharomyces cerevisiae* was inoculated therein as a γ-DD lactone-producing microorganism, followed by stationary culture at 25° C. for 4 days.

Further, another 10% bran suspension was treated with enzymes and sterilized by heating in the same manner as in Example 1, and Corynebacterium sp. NK-1 was inoculated therein as a γ-lactone-producing microorganism, followed by spinner culture under aeration for 5 days.

After the culturing was completed, the obtained four kinds of cultures were sterilized by heating to 95° C. and mixed in equal amounts. The obtained mixture had a flavor of mature bran pickles and contained 0.25% propionic acid, 0.04% γ-dodecalactone and 0.03% γ-dodecelactone.

Cucumbers were pickled in a solution prepared by diluting said mixture 10 times (solution of the present invention) and in a commercially available bran pickles flavoring solution (commercial solution 1) according to the method described in Example 1, and evaluation of the pickled cucumbers was made in respect of the same qualities by 12 panelists each having 7 points on each quality.

The results are shown in Table 4.

TABLE 4

|  | Mature flavor | Bran pickles flavor | Desirability as bran pickles |
| --- | --- | --- | --- |
| Solution of the present inv. | 4.62 ± 1.00 | 4.56 ± 0.98 | 4.56 ± 1.43 |
| Commercial solution 1 | 2.81 ± 1.36 | 2.67 ± 1.11 | 2.09 ± 0.87 |

As shown in Table 4, the solution of the present invention gave pickles superior to those obtained by using commercial solution 1 in all of the evaluated qualities, i.e. mature flavor, bran pickles flavor and desirability as bran pickles.

EXAMPLE 5

After a 10% bran suspension was treated with enzymes and sterilized by heating in the same manner as in Example 1, *Lactobacillus plantarum* was inoculated therein as a lactic acid-producing bacterium, followed by stationary culture at 25° C. for 2 days.

Separately, a 10% bran suspension was treated with enzymes and sterilized by heating in the same manner as in Example 1, and *Lactobacillus plantarum* was inoculated therein as a lactic acid-producing bacterium, followed by stationary culture at 25° C. for 2 days. Further, *Propionibacterium freudenreichii* was inoculated therein as a propionic acid-producing bacterium, followed by stationary culture at 25° C. for 7 days.

Another 10% bran suspension was treated with enzymes and sterilized by heating in the same manner as in Example 1, and *Enterococcus faecalis* was inoculated therein as a lactic acid-producing bacterium, followed by stationary culture at 25° C. for 2 days. Further, *Zygosaccharomyces bailii* was inoculated therein, followed by stationary culture at 25° C. for 4 days.

Further, another 10% bran suspension was treated with enzymes and sterilized by heating in the same manner as in Example 1, and *Enterococcus faecalis* was inoculated therein as a lactic acid-producing bacterium, followed by stationary culture at 25° C. for 2 days. Then, *Zygosaccharomyces bailii* was inoculated therein as a γ-DD lactone-producing microorganism, followed by spinner culture under aeration for 5 days.

After the culturing was completed, the obtained four kinds of cultures were sterilized by heating to 95° C. and mixed in equal amounts. The obtained mixture had a flavor of mature bran pickles and contained 0.20% propionic acid, 0.03% γ-dodecalactone and 0.02% γ-dodecelactone.

Cucumbers were pickled in a solution prepared by diluting said mixture 10 times (solution of the present invention) and in a commercially available bran pickles flavoring solution (commercial solution 1) according to the method described in Example 1, and evaluation of the pickled cucumbers was made in respect of the same qualities by 12 panelists each having 7 points on each quality.

The results are shown in Table 5.

TABLE 5

|  | Mature flavor | Bran pickles flavor | Desirability as bran pickles |
| --- | --- | --- | --- |
| Solution of the present inv. | 4.33 ± 1.40 | 4.00 ± 0.89 | 4.19 ± 1.21 |
| Commercial solution 1 | 2.45 ± 1.17 | 2.03 ± 1.32 | 2.01 ± 1.31 |

As shown in Table 5, the solution of the present invention gave pickles superior to those obtained by using the commercial solution in all of the evaluated qualities, i.e. mature flavor, bran pickles flavor and desirability as bran pickles.

EXAMPLE 6

To a 10% bran suspension was added castor oil to a concentration of 1%, and the resulting mixture was treated with enzymes and sterilized by heating in the same manner as in Example 1. Then, Corynebacterium sp. NK-1 was inoculated in the mixture, followed by spinner culture under aeration for 4 days.

As a result, a culture containing 692 ppm γ-dodecalactone, 243 ppm γ-dodecelactone and 572 ppm γ-decalactone was obtained.

EXAMPLE 7

To a medium (0.1% yeast extract, 0.5% peptone, 2% skim milk) containing 4% corn oil was added lipase in an amount of 1% based on the corn oil, followed by reaction at 37° C. for 10 hours to obtain corn oil hydrolysate. After the obtained corn oil hydrolysate was sterilized by heating, Corynebacterium sp. NK-1 was inoculated therein, followed by spinner culture under aeration for 5 days.

As a result, a culture containing 1850 ppm γ-dodecalactone and 558 ppm γ-dodecelactone was obtained.

EXAMPLE 8

Bran paste (5 kg) comprising 50% rice bran, 47% water and 3% sodium chloride was stirred and then fermented at 15° C. for 3 weeks, during which 5 cucumbers were pickled in the bran paste every day and taken out on the following day. The resulting fermented bran paste was divided into 2 portions, and one portion was inoculated with cultured cells of Corynebacterium sp. NK-1 in an amount of 0.1%. Then, each portion was stirred and then fermented at 15° C. for 2 weeks, during which 5 cucumbers were pickled in each bran paste every day and taken out on the following day. As a result, γ-dodecalactone and γ-dodecelactone were detected in a total amount of 32 ppm in the cell-inoculated bran paste, which had a good flavor, while γ-dodecalactone or γ-dodecelactone was not detected in the bran paste without incubation of the cells.

EXAMPLE 9

Bran paste (2 kg) comprising 50% rice bran, 47% water and 3% sodium chloride was stirred and then fermented at 15° C. for 3 weeks, during which 5 cucumbers were pickled in the bran paste every day and taken out on the following day. To the resulting fermented bran paste was added the mixture obtained in Example 3 (a bran pickles flavoring solution) in an amount of 10%, followed by mixing, and 5 cucumbers were pickled in the resulting bran paste. The pickled cucumbers had a good flavor of bran pickles.

EXAMPLE 10

After a 10% bran suspension was treated with enzymes and sterilized by heating in the same manner as in Example 1, *Lactobacillus plantarum* was inoculated therein as a lactic acid-producing bacterium, followed by stationary culture at 25° C. for 2 days. Then, *Saccharomyces cerevisiae* was inoculated therein as a γ-DD lactone-producing yeast, followed by spinner culture under aeration at 25° C. for 4 days.

Separately, a 2% bran suspension was treated with enzymes in the same manner as in Example 1, and fermented lactic acid was added thereto in an amount of 2%. After the resulting mixture was sterilized by heating, *Propionibacterium freudenreichii* was inoculated therein as a propionic acid-producing bacterium, followed by stationary culture at 25° C. for 6 days.

After the culturing was completed, both cultures were mixed. The obtained mixture (solution of the present invention 1) had a flavor of mature bran pickles and contained 3611 ppm propionic acid, 154 ppm γ-dodecalactone and 358 ppm γ-dodecelactone.

Said mixture (30 l) was filtered by means of a filter press pilot (Yabuta Kikai Co., Ltd.) to obtain the filtrate containing propionic acid. Then, 10 l of an aqueous solution containing 59% (v/v) ethanol (pH 4.7) was circulated through the residue for extraction. The obtained extract was mixed with the above filtrate to give a concentrated clear bran pickles flavoring solution (solution of the present invention 2) which had the turbidity of 0.021 at 660 nm and contained 2544 ppm propionic acid, 25.2 ppm γ-dodecalactone and 60.1 ppm γ-dodecelactone.

Measurements were made on solutions of the present invention 1 and 2 and commercially available bran pickles flavoring solutions (commercial solutions 1, 2 and 3) in respect of turbidity and content of components related to a bran pickles flavor. The turbidity is expressed in terms of the turbidity at 660 nm when each solution is diluted 10 times with water, and the content of flavoring components is expressed in terms of the concentration in each solution undiluted.

The results are shown in Table 6.

TABLE 6

| | Dilution | Turbidity (660 nm) | Propionic acid (ppm) | γ-Dodeca lactone + γ-dodece-lactone (ppm) |
|---|---|---|---|---|
| Solution of the present inv. 1 | 10–20 times | 3.51 | 3611 | 512.0 |
| Solution of the present inv. 2 | 10–20 times | 0.001 | 2544 | 85.3 |
| Commercial solution 1 | 7–10 times | 0.008 | tr | 1.4 |
| Commercial solution 2 | 7–10 times | 9.41 | 422 | tr |
| Commercial solution 3 | 20–40 times | 0.056 | tr | tr | tr: trace

Sensory evaluation was made on the cucumber pickles prepared by using solutions of the present invention 1 and 2 and commercial solutions 1, 2 and 3. Each of the solutions was diluted 10 times, and lactic acid, sodium chloride and sodium glutamate were added thereto to the concentrations of 0.5%, 2.5% and 0.62%, respectively, to prepare a pickling solution. In the obtained solution were pickled cucumbers which had been previously pickled in a 6% aqueous solution of sodium chloride at 5° C. for one day. After pickling at 5° C. for 2 days, the pickling solution was removed and the cucumbers were cut. Evaluation of the cut cucumbers was made in respect of mature flavor, bran pickles flavor and desirability as bran pickles by 11 panelists each having 7 points on each quality.

The results are shown in Table 7.

TABLE 7

| | Mature flavor | Bran pickles flavor | Desirability as bran pickles |
|---|---|---|---|
| Solution of the present inv. 1 | 5.12 ± 0.65* | 5.21 ± 1.09* | 4.50 ± 1.56* |
| Solution of the present inv. 2 | 5.09 ± 1.45* | 5.36 ± 1.12* | 5.27 ± 0.90* |
| Commercial solution 1 | 2.82 ± 1.25 | 2.45 ± 1.13 | 2.91 ± 1.87 |
| Commercial solution 2 | 3.55 ± 1.13 | 3.09 ± 1.51 | 2.27 ± 1.19 |
| Commercial solution 3 | 2.09 ± 1.30 | 2.00 ± 1.34 | 2.36 ± 1.12 |

*: $p < 0.01$

As shown in Table 7, the solutions of the present invention gave pickles superior to those obtained by using the commercial solutions in all of the above qualities, i.e. mature flavor, bran pickles flavor and desirability as bran pickles.

EXAMPLE 11

A pickling solution was prepared from solution of the present invention 2 obtained in Example 10 in the same manner as in Example 10, and cut cucumbers were pickled therein at 5° C. for 30 minutes. As a result, lightly pickled cucumbers having a flavor of bran pickles were obtained. Cucumber pickles prepared by sprinkling the above solution over cut cucumbers also had a flavor of bran pickles.

EXAMPLE 12

A 10% bran suspension was treated with enzymes and sterilized by heating in the same manner as in Example 1, and *Lactobacillus plantarum* was inoculated therein as a lactic acid-producing bacterium, followed by stationary culture at 25° C. for 3 days. Then, *Saccharomyces cerevisiae* was inoculated therein as a γ-DD lactone-producing yeast, followed by spinner culture under aeration at 25° C. for 4 days to obtain a culture containing γ-dodecalactone and γ-dodecelactone in a total amount of 2872 ppm. Separately, a 3% bran suspension was treated with enzymes in the same manner as in Example 1, and fermented lactic acid was added thereto in an amount of 3%. After the resulting mixture was sterilized by heating, *Propionibacterium freudenreichii* was inoculated therein as a propionic acid-producing bacterium, followed by stationary culture at 25° C. for 7 days to obtain a culture containing 2.51% propionic acid. Both cultures thus obtained were mixed, and lactic acid, sodium chloride and sodium glutamate were added thereto to the concentrations of 0.5%, 2.5% an 0.62%, respectively. From this mixture were prepared pickling solutions containing propionic acid, γ-dodecalactone and γ-dodecelactone at the concentrations shown in Table 8. In each of the pickling solutions (adjusted to pH 4.5) were pickled cucumbers which had been previously pickled in a 6% aqueous solution of sodium chloride at 5° C. for one day. After pickling at 5° C. for 2 days, the pickling solution was removed and the cucumbers were sliced. Evaluation of the sliced cucumbers was made in respect of bran pickles flavor and desirability as bran pickles by 9 panelists, in which each quality was evaluated into 4 grades.

The bran pickles flavor was evaluated into the following 4 grades: –, weak; +, rather strong; ++, strong; and +++, very strong. The desirability as bran pickles was evaluated into the following 4 grades: –, little desirable; +, rather desirable; ++, desirable; and +++, highly desirable.

The average values of the evaluation are shown in Table 8.

TABLE 8

| Propionic acid (ppm) | γ-Dodecalactone + γ dodecelactone (ppm) | Bran pickles flavor | Desirability as bran pickles |
|---|---|---|---|
| 0 | 0 | − | − |
| 0 | 100 | − | − |
| 20 | 100 | − | − |
| 50 | 100 | + | + |
| 100 | 100 | + + | + + |
| 250 | 100 | + + | + + |
| 500 | 100 | + + | + + + |
| 1000 | 100 | + + + | + + + |
| 2000 | 100 | + | + + + |
| 3000 | 100 | + | + + |
| 4000 | 100 | − | + + |
| 500 | 0 | − | − |
| 500 | 5.0 | − | − |
| 500 | 10.0 | + | + |
| 500 | 25.0 | + + | + + |
| 500 | 100.0 | + + | + + + |
| 500 | 200.0 | + + + | + + + |
| 500 | 300.0 | + + | + |
| 500 | 400.0 | − | − |

EXAMPLE 13

A culture of a propionic acid-producing bacterium prepared in the same manner as in Example 12 (30 l) was filtered by means of a filter press pilot (Yabuta Kikai Co., Ltd.) to obtain the filtrate containing propionic acid.

Separately, a culture of a γ-DD lactone-producing yeast prepared in the same manner as in Example 12 (30 l) was filtered by means of a filter press pilot (Yabuta Kikai Co., Ltd.), and 10 l of an aqueous solution containing 59% (v/v) ethanol (pH 4.7) was circulated through the residue for extraction to obtain a 1151 ppm lactone solution. The obtained lactone solution was mixed with the above filtrate, and lactic acid, sodium chloride and sodium glutamate were added thereto to the concentrations of 0.5%, 2.5% and 0.62%, respectively. From this mixture were prepared pickling solutions containing propionic acid, γ-dodecalactone and γ-dodecelactone at the concentrations shown in Table 9. In each of the pickling solutions (adjusted to pH 4.5) were pickled cucumbers which had been previously pickled in a 6% aqueous solution of sodium chloride at 5° C. for one day. After pickling at 5° C. for 2 days, the pickling solution was removed and the cucumbers were sliced. Evaluation of the sliced cucumbers was made in respect of bran pickles flavor and desirability as bran pickles by 14 panelists. The qualities were evaluated into 4 grades in the same manner as in Example 12.

The average values of the evaluation are shown in Table 9.

TABLE 9

| Propionic acid (ppm) | γ-Dodecalactone + γ-dodecelactone (ppm) | Bran pickles flavor | Desirability as bran pickles |
|---|---|---|---|
| 0 | 0 | − | − |
| 0 | 17.5 | − | − |
| 20 | 17.5 | − | − |
| 50 | 17.5 | + | + |
| 100 | 17.5 | + + | + + |
| 250 | 17.5 | + + | + + |

TABLE 9-continued

| Propionic acid (ppm) | γ-Dodecalactone + γ-dodecelactone (ppm) | Bran pickles flavor | Desirability as bran pickles |
|---|---|---|---|
| 500 | 17.5 | + + + | + + + |
| 1000 | 17.5 | + + | + + + |
| 2000 | 17.5 | + | + + |
| 3000 | 17.5 | − | + |
| 360 | 17.5 | + + | + + |
| 360 | 0 | − | − |
| 360 | 1.0 | − | − |
| 360 | 2.0 | + | + |
| 360 | 4.0 | + + | + + |
| 360 | 17.5 | + + + | + + + |
| 360 | 70.0 | + + + | + + + |
| 360 | 150.0 | + + | + |
| 360 | 200.0 | + | − |

EXAMPLE 14

A culture containing γ-dodecalactone and γ-dodecelactone in a total amount of 1540 ppm as bran pickles flavoring components was filtered by pressure, and a half portion of the residue was extracted with 0–50 vol % aqueous solutions of ethanol. As a result, γ-dodecalactone and γ-dodecelactone were recovered when the ethanol concentration was 10 vol % or higher, and the recovery yield was remarkably enhanced by the use of a solution having the ether concentration of 30 vol % or higher (refer to FIG. 1).

Figure 2:
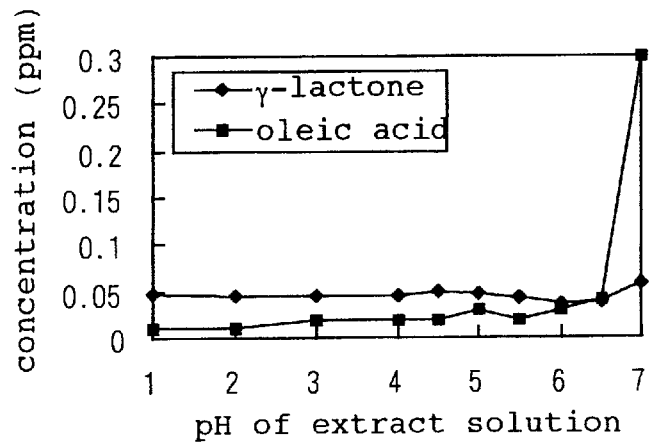
FIG. 2 is a graph showing the pH of the solution used for extraction and the concentrations of extracted γ-lactone and oleic acid.

The other half portion of the residue was extracted with 35% aqueous solutions of ethanol varied in pH to measure the amount of fatty acids extracted. As a result, extraction of fatty acids was suppressed at pH 6.5 or lower (refer to FIG. 2).

Figure 3:
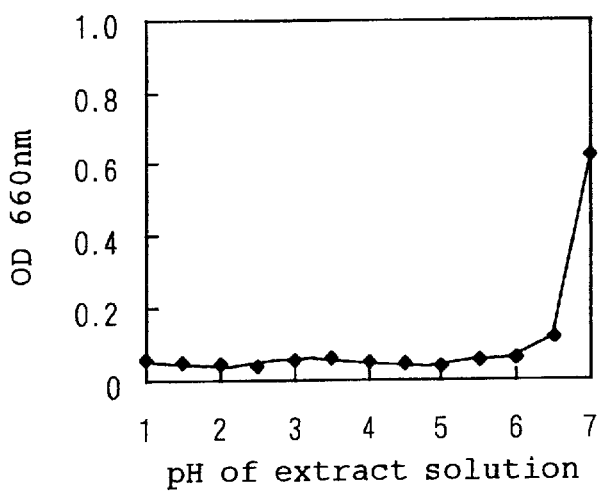
FIG. 3 is a graph showing the pH of the solution used for extraction and the turbidity of the bran pickles flavoring solution.

Said extracts were respectively mixed with the filtrate obtained by filtration to prepare clear bran pickles flavoring solutions. Each of the resulting solutions was diluted 10 times with water, and the turbidity was measured. As a result, it was demonstrated that when the aqueous solution of ethanol is acidic, specifically at pH 6.5 or lower, the turbidity of a bran pickles flavoring solution is low and a clear bran pickles flavoring solution having a good flavor can be prepared (refer to FIG. 3).

INDUSTRIAL APPLICABILITY

The present invention provides processes for producing the following: a novel bran pickles flavoring solution, a novel clear bran pickles flavoring solution, pickles made by pickling foods in said flavoring solutions, lactones which are essential components of said flavoring solutions, and rice bran paste containing said lactones.

What is claimed is:

1. A biolgically pure culture of Corynebacterium sp. NK-1 (FERM BP-6329).

* * * * *